US007354994B2

(12) United States Patent
Sumner et al.

(10) Patent No.: US 7,354,994 B2
(45) Date of Patent: Apr. 8, 2008

(54) RECOMBINANT IGF EXPRESSION SYSTEMS

(76) Inventors: Emma Jayne Sumner, PO Box 2, Belasis Avenue, Billingham, TS23 1YN (GB); Ian Hodgson, PO Box 2, Belasis Avenue, Billingham, TS23 1YN (GB)

( * ) Notice: Subject to any disclaimer, the term of this patent is extended or adjusted under 35 U.S.C. 154(b) by 352 days.

(21) Appl. No.: 10/866,086

(22) Filed: Jun. 14, 2004

(65) Prior Publication Data
US 2005/0095672 A1    May 5, 2005

Related U.S. Application Data

(60) Provisional application No. 60/477,941, filed on Jun. 13, 2003.

(51) Int. Cl.
*A61K 38/30* (2006.01)
*C07K 14/65* (2006.01)
*C12P 21/02* (2006.01)

(52) U.S. Cl. .................. 530/303; 514/12; 530/324; 435/69.1

(58) Field of Classification Search ................ 530/303, 530/324; 514/12; 435/69.1
See application file for complete search history.

(56) References Cited

U.S. PATENT DOCUMENTS

| 5,470,727 A | 11/1995 | Mascarenhas et al. |
| 5,629,172 A | 5/1997 | Mascarenhas et al. |
| 6,068,994 A | 5/2000 | Barr |

FOREIGN PATENT DOCUMENTS

| WO | WO 96/40722 A | 12/1996 |
| WO | WO 9640722 A1 * | 12/1996 |

OTHER PUBLICATIONS

Definition of "juxtaposed," Merriam-Webster Online Dictionary, http://www.m-w.com/dictionary/juxtaposed, printed on Jan. 19, 2007.*
Olson et al., "High-Level Expression of Eukaryotic Polypeptides from Bacterial Chromosomes," *Protein Expression and Purification*, Nov. 1998, pp. 160-166, vol. 14, No. 2.
Baker, "Protein expression using ubiquitin fusion and cleavage,"*Current Opinion in Biotechnology*, Oct. 1996, pp. 541-546, vol. 7, No. 5.
Belagaje et al., "Increased production of low molecular weight recombinant proteins in *Escherichia coli*," *Protein Science*, 1997, pp. 1953-1962, vol. 6, Cambridge University Press, USA.
Bernardi et al. (Ed.), "Nomenclature for incompletely specified bases in nucleic acid sequences," *Eur. J. Biochem*, 1985, pp. 1-5, vol. 150, FEBS.
Buell et al., "Optimizing the expression in *E. coli* of a synthetic gene encoding somatomedin-C (IGF-I),"*Nucleic Acids Research*, 1985, pp. 1923-1939, vol. 13, No. 6, IRL Press Limited, Oxford England.
Heding et al., "Biosensor Measurement of the Binding of Insulin-like Growth Factors I and II and Their Analogues to the Insulin-like Growth Factor-binding Protein-3," *The Journal of Biological Chemistry*, Jun. 14, 1996, pp. 13948-13952, vol. 271, No. 24, The American Society for Biochemistry and Molecular Biology, Inc., USA.
Kotyk, *Quantities, Symbols, Units, and Abbrevations in the Life Sciences, A Guide for Authors and Editors*, 1999, Table of Contents Only, Humana Press, Inc., Totowa, New Jersey, USA.
Olson et al., "High-Level Expression of Eukaryotic Polypeptides from Bacterial Chromosomes," *Protein Expression and Purification*, 1998, pp. 160-166, vol. 14, Article No. PT980973, Academic Press.
Sambrook et al. (Eds.), *Molecular Cloning, A Laboratory Manual*, 2nd Edition, 1989, Table of Contents Only, Cold Spring Harbor Laboratory Press.
Schoner et al., "Isolation and Purification of Protein Granules from *Escherichia coli* Cells Overproducing Bovine Growth Hormone," *Bio/Technology*, Feb. 1985, pp. 151-154.
Schulz et al., "Increased Expression in *Escherichia coli* of a Synthetic Gene Encoding Human Somatomedin C after Gene Duplication and Fusion," *Journal of Bacteriology*, Dec. 1987, pp. 5385-5392, vol. 169, No. 12, American Society for Microbiology.
Stanway et al., "The complete nucleotide sequence of a common cold virus: human rhinovirus 14," *Nucleic Acids Research*, 1984, pp. 7859-7875, vol. 12, No. 20.
Warrens et al., "Splicing by overlap extension by PCR using asymmetric amplification: an improved technique for the generation of hybrid proteins of immunological interest," *Gene*, 1997, pp. 29-35, vol. 186, Elsevier Science B.V.
Williams et al., "Cytoplasmic Inclusion Bodies in *Escherichia coli* Producing Biosynthetic Human Insulin Proteins," *Science*, Feb. 5, 1982, pp. 687-689, vol. 215.
Zhang et al., "Expression of Eukaryotic Proteins in Soluble Form in *Escherichia coli*," *Protein Expression and Purification*, 1998, pp. 159-165, vol. 12, Article No. PT9700834, Academic Press.

* cited by examiner

*Primary Examiner*—Jon Weber
*Assistant Examiner*—Rosanne Kosson
(74) *Attorney, Agent, or Firm*—Foley & Lardner LLP

(57) ABSTRACT

The present invention provides nucleic acid sequences, expression systems, host cells, polypeptides and methods of producing mature insulin-like growth factor (IGF) using a fusion construct which yields high levels of fusion proteins that are easily processed to provide IGF with a proper N-terminus.

13 Claims, 6 Drawing Sheets

Figure 1

Nucleic Acid Sequence of IGF-1

GGTCCGGAAACCCTGTGCGGTGCTGAACTGGTTGACGCTCTGCAGTTCGTTTGCGGTGACCGTGGTTCTACTTCAACAAACCG
ACGGGTTACGGTTCCTCCTCCCGTCGTGCTCCGCAGACCGGTATCGTTGACGAATGCTGCTTCCGGTCCTGCGACCTGCGTCGTC
TGGAAATGTACTGCGCTCCGCTGAAACCGGCTAAATCCGCTTAA

Amino Acid Sequence Of Human IGF-1

GPETLCGAELVDALQFVCGDRGFYFNKPTGYGSSSRRAPQTGIVDECCFRSCDLRRLEMYCAPLKPAKSA*

Figure 2

Amino Acid sequence of fusion proteins constructed and tested

| Clone | SEQ.ID.NO. | Sequence |
|---|---|---|
| Met-3C-IGF | 14 | MLEVLFQ^GPETLCGAELVDALQFVCGDRGFYFNKPTGYGSSSRRAPQTGIVDECCFRSCDLRR LEMYCAPLKPAKSA |
| LacZ-3C-IGF | 15 | MITPSLHACRFSTLEDPRVPSSNSLEVLFQ^GPETLCGAELVDALQFVCGDRGFYFNKPTGYGS SSRRAPQTGIVDECCFRSCDLRRLEMYCAPLKPAKSA |
| Ubi-IGF | 16 | MQIFVKTLTGKTITLEVESSDTIDNVKSKIQDKEGIPPDQQRLIFAGKQLEDGRTLSDYNIQKE STLHLVLRLRGG^GPETLCGAELVDALQFVCGDRGFYFNKPTGYGSSSRRAPQTGIVDECCFRS CDLRRLEMYCAPLKPAKSA |
| UBI-3C-IGF | 17 | MQIFVKTLTGKTITLEVESSDTIDNVKSKIQDKEGIPPDQQRLIFAGKQLEDGRTLSDYNIQKE STLHLVLRLRGGLEVLFQ^GPETLCGAELVDALQFVCGDRGFYFNKPTGYGSSSRRAPQTGIVD ECCFRSCDLRRLEMYCAPLKPAKSA |
| Tr41 Ubi-3C-IGF | 18 | MQIFVKTLTGKTITLEVESSDTIDNVKSKIQDKEGIPPDQQLEVLFQ^GPETLCGAELVDALQF VCGDRGFYFNKPTGYGSSSRRAPQTGIVDECCFRSCDLRRLEMYCAPLKPAKSA |
| Tr17 Ubi-3C-IGF | 19 | MQIFVKTLTGKTITLEVLEVLFQ^GPETLCGAELVDALQFVCGDRGFYFNKPTGYGSSSRRAPQ TGIVDECCFRSCDLRRLEMYCAPLKPAKSA |
| Tr11 Ubi-3C-IGF | 20 | MQIFVKTLTGKLEVLFQ^GPETLCGAELVDALQFVCGDRGFYFNKPTGYGSSSRRARQTGIVDE CCFRSCDLRRLEMYCAPLKPAKSA |

^ = cleavage juncture between fusion protein and IGF

Figure 3

| Clone | Total Mass | Fusion Mass | IGF Mass | Disposition | Shake Flask Total expression (g/L) | Shake Flask IGF expression (g/L) | % increase IGF expression | 3C cleavage |
|---|---|---|---|---|---|---|---|---|
| Met-3C-IGF | 8534 | 879 | 7655 | 100% insoluble | < 0.005 | nd | | nd |
| LacZ-3C-IGF | 11031 | 3376 | 7655 | 100% insoluble | < 0.005 | nd | | nd |
| Ubi-IGF | 16212 | 8557 | 7655 | 50:50 soluble/insoluble | 0.08 | N/A | | N/A |
| UBI-3C-IGF | 16942 | 9287 | 7655 | 50:50 soluble/insoluble | 0.07 | 0.036 | -4 % | Yes |
| Tr41 Ubi-3C-IGF | 12961 | 5306 | 7655 | 100% insoluble | 0.11 | 0.065 | 72 % | Yes |
| Tr17 Ubi-3C-IGF | 10307 | 2652 | 7655 | 100% insoluble | 0.12 | 0.089 | 136 % | No* |
| Tr11 Ubi-3C-IGF | 9650 | 1995 | 7655 | 100% insoluble | 0.11 | 0.087 | 131 % | No* | nd = Not determined n/a = Not applicable

* = Extreme insolubility requires high concentration of chaotrope. The samples were not sufficiently diluted and the 3C protease was inactivated by the chaotrope.

RECOMBINANT IGF EXPRESSION SYSTEMS

This application claims the benefit of U.S. Provisional Application No. 60/477,941, filed Jun. 13, 2003, which is herein incorporated by reference.

BACKGROUND OF THE INVENTION

1. Field of the Invention

The present invention provides recombinant insulin-like growth factor (IGF) expression systems that yield high levels of product which are easily processed to provide IGF with a proper N-terminus for human use.

2. Description of the Related Art

Recombinant production allows the large scale manufacturing of therapeutic proteins while avoiding many of the difficulties and hazards of protein purification from natural sources. In the case of human proteins, recombinant manufacturing is frequently the only practical method for producing the amounts of protein required for commercial sales of therapeutic products. Recombinant production also eliminates worker exposure to human fluid and tissues, avoiding potential exposure to infectious agents such as viruses.

Recombinant manufacturing involves the expression of a DNA construct encoding for the desired protein in a recombinant host cell. The host cell can be either prokaryotic (e.g., bacteria such as *Escherichia coli*) or eukaryotic (e.g., yeast or mammalian cell-line). For large scale recombinant manufacturing, bacterial or yeast host cells are most commonly used, due to the ease of manipulation and growth of these organisms and also because these organisms require relatively simple growth media.

Recombinant manufacturing, however, does have its difficulties. Expression constructs must be optimized for a particular protein and for a particular host cell. Expressing a recombinant protein in a host cell exposes the recombinant protein to a new set of host cell enzymes, such as proteases, which can modify or even degrade the recombinant protein. Modification and degradation of the recombinant protein is undesirable, as it decreases yields and can complicate the purification of the recombinant protein. Polypeptides overexpressed in the bacterial cytoplasm often accumulate as insoluble "inclusion bodies" (Williams et al., *Science* 215: 687-688 (1982); Schoner et al., *Biotechnology* 3:151-154 (1985)). Polypeptides accumulated in the form of inclusion bodies are relatively useless. Conversion of this insoluble material into active, soluble polypeptide requires slow and difficult solubilization and refolding protocols that often greatly reduce the net yield of biologically active polypeptide. This problem has particularly impacted the production of IGF, resulting in numerous attempts to solve the "refolding problem." Even when polypeptides are expressed in the cytoplasm of bacteria in soluble form, they often accumulate poorly as a result of degradation by host proteases. Furthermore, the accumulated polypeptides often lack the desired amino terminus. This problem is commonly addressed by the expression of a fusion protein, in which the N-terminus of the desired polypeptide is fused to a carrier protein.

However, the use of fusion polypeptides has drawbacks. It is often necessary to cleave the desired polypeptide away from the fusion partner by enzymatic or chemical means. This can be accomplished by placing an appropriate target sequence for cleavage between the fusion partner and the desired polypeptide. Unfortunately, the enzymes most widely used for polypeptide cleavage are expensive, inefficient, or imprecise in their cleavage and cannot be successfully applied to a majority of fusion constructs. For example, enterokinase and Factor Xa are mammalian enzymes that are expensive to produce and exhibit highly variable cleavage efficiency. Meanwhile, enzymes like subtilisin are relatively inexpensive to produce, but their precision is unacceptable for commercial-scale processes under current "Good Manufacturing Practices" (GMP). The human rhinovirus 14 protease, termed 3C protease, is a robust, precise, and inexpensive enzyme that cleaves the amino acid sequence E-(V or T)-L-F-Q-G-P (SEQ ID NO: 22) immediately N-terminal to the glycine residue. 3C protease has been used to cleave IGF from dsbA-IGF fusion constructs (Olson et al., *Protein Expr Purif.* 14:160-166 (1998)). As a substantial portion of the dsbA-IGF is refractory to cleavage, however, 3C protease may not be universally applicable to 3C site containing IGF fusion constructs.

The patent literature describes numerous fusion systems for the production of IGF, each of which has certain advantages and disadvantages. For example, constructs encoding native mature IGF-1 (with an additional methionine) yield low expression levels. A variety of approaches were developed to enhance expression, including the use of fusion partners (Schulz M. F. et al., *J. Bact.* 169:585-53921(1987)), and the use of multiple protease-deficient hosts (Buell et al., *Nucleic Acids Res.* 13:1923-1938 (1985)). However, the growth characteristics of these protease deficient hosts are not ideal for high intensity fermentation. It also has been found that good expression can be obtained simply by adding Met-Arg-Lys to the N-terminus, but this does not produce authentic IGF-1 (Belagaje et al. *Protein Sci.* 6:1953-19623 (1997)).

An additional problem that is often overlooked when designing IGF fusion constructs is that the fusion partner is essentially a waste product. Prokaryotes can express only a finite amount of recombinant protein—typically up to 40% of the dry mass of the cell. If the fusion partner is a large protein relative to the IGF, then the effective amount of IGF is reduced. For example, dsbA-IGF fusion proteins are approximately 31,500 daltons, of which the IGF is approximately 7,500 daltons, or approximately 24 percent of the total fusion protein. See U.S. Pat. No. 5,629,172. Thus, the efficiency of IGF protein production can be enhanced by using a proportionally smaller fusion partner.

Identifying an effective fusion partner is a difficult task that typically involves significant trial and error. Therefore, improved constructs with more effective fusion partners are required to enhance the production of recombinant IGF.

SUMMARY OF THE INVENTION

According to certain aspects of the invention, therefore, there are provided nucleic acid sequences, expression systems, host cells, polypeptides, and methods of producing recombinant insulin-like growth factor (IGF).

In one embodiment, the present invention provides for a nucleic acid sequence encoding the polypeptide sequence:

MQIFVKTLTGK[$X^1$]$_{0-30}$LE[$X^2$]LFQ [IGF]   (SEQ ID NO: 23)

wherein $X^1$ is a peptide sequence from 0 to 30 amino acids; $X^2$ is either V or T; and IGF is N-terminal IGF-I. In other embodiments, the present invention provides a nucleic acid encoding the above polypeptide, wherein $X^1$ is TITLEV (SEQ ID NO. 24),

TITLEVESSDTIDNVKSKIQDKEGIPPDQQ (SEQ ID NO:25), or represents no (i.e. zero) amino acid.

In another embodiment, the present invention provides for a protein expression vector encoding the polypeptide sequence:

MQIFVKTLTGK[X$^1$]$_{0-30}$LE[X$^2$]LFQ [IGF]   (SEQ ID NO: 23)

wherein X$^1$ is a peptide sequence from 0 to 30 amino acids; X$^2$ is either V or T; and IGF is N-terminal IGF-I. In other embodiments, the present invention provides a protein expression vector encoding the above polypeptide, wherein X$^1$ is TITLEV (SEQ ID NO: 24),

TITLEVESSDTIDNVKSKIQDKEGIPPDQQ (SEQ ID NO:25), or represents no (i.e. zero) amino acid.

In another embodiment, the present invention provides for a protein of the sequence:

MQIFVKTLTGK[X$^1$]$_{0-30}$LE[X$^2$]LFQ [IGF]   (SEQ ID NO: 23)

wherein X$^1$ is a peptide sequence from 0 to 30 amino acids; X$^2$ is either V or T; and IGF is N-terminal IGF-I. In other embodiments, the present invention provides a protein of the above sequence, wherein X$^1$ is TITLEV (SEQ ID NO: 24),

TITLEVESSDTIDNVKSKIQDKEGIPPDQQ (SEQ ID NO:25), or represents no (i.e. zero) amino acid.

In yet another embodiment, the present invention provides recombinant host cells expressing a protein of the sequence:

MQIFVKTLTGK[X$^1$]$_{0-30}$LE[X$^2$]LFQ [IGF]   (SEQ ID NO: 23)

wherein X$^1$ is a peptide sequence from 0 to 30 amino acids; X$^2$ is either V or T; and IGF is N-terminal IGF-I. In other embodiments, the present invention provides a protein of the above sequence, wherein X$^1$ is TITLEV (SEQ ID NO 24),

TITLEVESSDTIDNVKSKIQDKEGIPPDQQ (SEQ ID NO:25), or represents no (i.e. zero) amino acid. In one embodiment, the host cells are prokaryotic. In another embodiment, the host cells are eukaryotic.

In another embodiment, the present invention provides for a method of expressing IGF, comprising transfecting a host cell with the expression vector described above, culturing those cells under conditions which permit protein expression and isolating the protein from the cells, supernatant or broth. In one embodiment, the expression vector encodes a protein of the above sequence, wherein X$^1$ is TITLEV (SEQ ID NO: 24),

TITLEVESSDTIDNVKSKIQDKEGIPPDQQ (SEQ ID NO:25), or represents no (i.e. zero) amino acid. In one embodiment, the host cells are prokaryotic, while in another, the host cells are eukaryotic.

The present invention also provides a method of preparing N-terminal IGF, wherein a cleavage mixture is prepared containing a chaotropic agent, 3C protease and a polypeptide of the sequence:

MQIFVKTLTGK[X$^1$]$_{0-30}$LE[X$^2$]LFQ [IGF]   (SEQ ID NO: 23)

wherein X$^1$ is a peptide sequence from 0 to 30 amino acids; X$^2$ is either V or T; and IGF is N-terminal IGF-I. In one aspect, the method employs a cleavage mixture containing a protein of the above sequence, wherein X$^1$ is TITLEV (SEQ ID NO: 24),

TITLEVESSDTIDNVKSKIQDKEGIPPDQQ (SEQ ID NO:25), or represents no (i.e. zero) amino acid. The cleavage mixture further contains a reducing agent, such as dithiothreitol.

Other objects, features and advantages of the present invention will become apparent from the following detailed description. The detailed description and specific examples, while indicating preferred embodiments, are given for illustration only since various changes and modifications within the spirit and scope of the invention will become apparent to those skilled in the art from this detailed description. Further, the examples demonstrate the principle of the invention and cannot be expected to specifically illustrate the application of this invention to all the examples where it will be obviously useful to those skilled in the prior art.

DESCRIPTION OF THE DRAWINGS

FIG. 1 provides the nucleic acid sequence (SEQ ID NO: 13) and the amino acid sequence (SEQ ID NO: 21) of human IGF.

FIG. 2 provides the amino acid sequences of seven IGF-I fusion constructs described herein (SEQ ID NO: 14 through SEQ ID NO: 20).

FIG. 3 sets forth a comparison of mass, expression disposition, expression yield, and protease cleavage of the seven IGF-I fusion constructs described herein.

DETAILED DESCRIPTION

Figure 4:
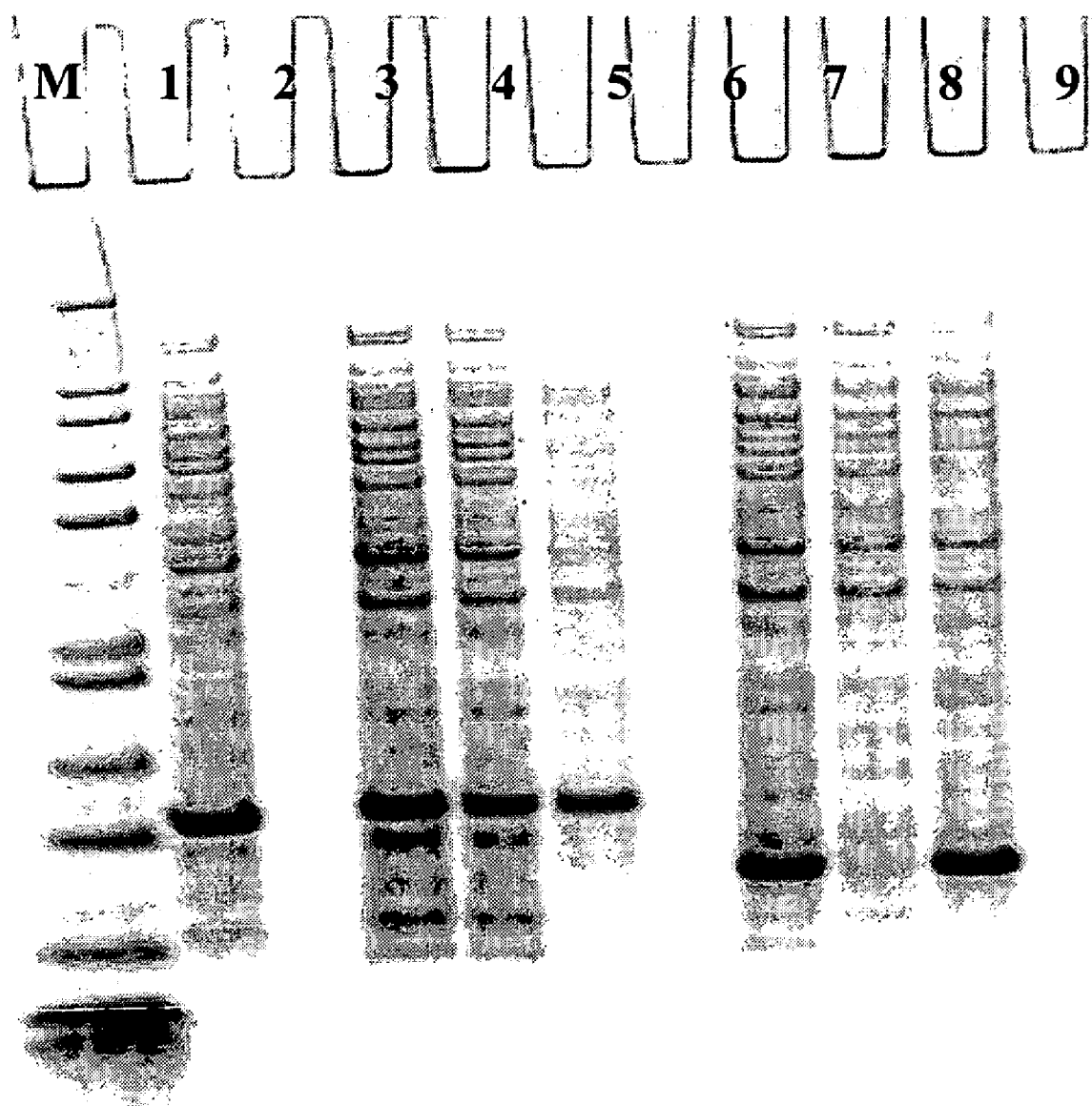
FIG. 4 depicts the soluble and insoluble properties of the full length Ubiquitin-3C-IGF and TR41 Ubi-3C-IGF proteins. A SDS-PAGE gel was loaded with the following: (M) molecular weight standards; (1) Ubiquitin-IGF standard; (2) empty lane; (3) full length ubiquitin-3C-IGF total cell extract; (4) full length ubiquitin-3C-IGF soluble cell extract; (5) full length ubiquitin-3C-IGF insoluble cell extract; (6) empty lane; (7) TR41 Ubi-3C-IGF total cell extract; (8) TR41 Ubi-3C-IGF soluble cell extract; and (9) TR41 Ubi-3C-IGF insoluble cell extract.

DNA constructs for making IGF are provided. The inventive constructs enhance production of IGF by dramatically improving the yield of expression systems employing fusion constructs comprising ubiquitin-derived peptides, a 3C protease cleavage site, and a N-terminal IGF.

In one embodiment, a short peptide sequence, composed of approximately 11 consecutive amino acids from the protein ubiquitin is used to provide high-level expression of IGF in *E. coli*. In another embodiment, a protease cleavage site from the 3C protein can be incorporated into IGF fusion constructs. In other embodiments, small proteins having a C-terminus with the sequence E-V/T-L-F-Q (SEQ ID NO: 26) can be fused in-frame with IGF. As the N-terminus of IGF begins with the amino acids G-P, the resulting fusion protein contains the protease cleavage site E-V/T-L-F-Q// G-P (SEQ ID NO: 22). The 3C protease recognizes this cleavage site (denoted here by "//") and releases IGF from the construct. Thus, in one aspect of the invention, there is provided a prokaryotic expression system for efficiently producing human IGF. Moreover, the inventive constructs and methods dramatically improve the yield of recombinant IGF.

Definitions

Unless defined otherwise, all technical and scientific terms used herein have the same meaning as is commonly understood by one of ordinary skill in the art to which this invention belongs. Likewise, the terminology used herein describes particular embodiments only, and is not intended to limit the scope of the invention.

Nucleic acid code and amino acid code may be expressed in single-letter designations as described by IUB Nomenclature Committee, *Eur. J Biochem.* 150:1-5 (1985), and incorporated herein by reference. Similarly, genes and proteins, such as restriction endonucleases, may be expressed in abbreviated forms that are well recognized in the art (Kotyk A., ed., *Quantities, Symbols, Units, and Abbreviations in the Life Sciences: A Guide for Authors and Editors*, Totowa, N. J., Humana Press (1999)).

As used herein, "N-terminal IGF" refers to a polypeptide encoding IGF-I, particularly human IGF-I, in which the first N-terminal two amino acids are Glycine (G) and Proline (P) respectively. N-terminal IGF includes, but is not limited to, full length IGF, C-terminal truncated forms of IGF, chimeras of N-terminal IGF and point mutants of IGF which do not modify the N-terminal amino acids G and P. Particular examples of N-terminal IGF are shown in the Figures alone or as members of complete fusion constructs. By way of further example, "N-terminal IGF" does not embrace a naturally occurring truncated form of IGF-I lacking the first three N-terminal amino acids (hereinafter "des(1-3)-IGF-I"). See Heding et al., *J. Biol. Chem.*, 271:13948-13952 (1996).

As used herein, "GP-IGF" refers to an IGF that has been cleaved from a fusion construct to yield a polypeptide with the proper amino terminal sequence of human IGF.

As used herein, "mature IGF" refers to a GP-IGF that has been refolded and optionally isolated such that it exhibits a useful biological property. The art recognizes utility in IGF molecules that stimulate cell or anabolic growth, (via agonist activity), IGF molecules that antagonize cell or anabolic growth (via antagonist activity or by displacing agonist IGF [so called "null IGF"]), and IGF molecules that bind to one or more Insulin Like Growth Factor Binding Proteins.

As used herein, "expression systems" refers to a single nucleic acid or a plurality of nucleic acids that are used to direct expression of a target nucleic acid or the production and/or assembly of a polypeptide. Expression systems of the present invention are not particularly limiting in their form and may be either plasmid based or may direct chromosomal integration of the target sequence. See Sambrook et al., *Molecular Cloning: A Laboratory Manual*, New York, Cold Spring Harbor Laboratory Press (1989); U.S. Pat. No. 5,470, 727.

As used herein, "host cells," in one embodiment, refer to bacteria, particularly *E. coli* host strains including K strains and B strains and their derivatives including protease deficient strains. In another embodiment, the term refers to eukaryotic cells, such as yeast or tissue culture cell line which have been immortalized for propagation in the laboratory. In yet another embodiment, the term refers to cells derived from animal, plant, fungal, or insect tissue.

As used herein, "3C protease" refers to a protease that recognizes the amino acid sequence E-(V or T)-L-F-Q-G-P (SEQ ID NO: 22). The protease cleaves the sequence N-terminal to the glycine. The designation "3C protease" is derived from the human rhinovirus 14 protease and known to those skilled in art as 3C. See Stanway et al., *Nucleic Acids Res.* 12:7859-75 (1984).

The following examples serve to illustrate various embodiments of the present invention and should not be construed, in any way, to limit the scope of the invention.

EXAMPLES

Example 1

Production of Ubiq-3C-IGF-1 Expression Vectors

The human IGF-1 gene containing a 5'3C protease cleavage site (hereinafter 3C-IGF-1) has been cloned into three expression vectors.

A. Cloning and Verification of Expression Vectors

Human IGF-1 (Celtrix Pharmaceuticals, Inc., Glen Allen, Va.), whose nucleotide and amino acids sequences are set forth in FIG. 1, was cloned with an oligonucleotide encoding the six amino acids of the 3C protease cleavage site plus methionine into vectors pET29a and pPop. This fusion strategy represents the smallest possible fusion partner for IGF-1 and was used to investigate protein accumulation and degradation.

3C-IGF-1 was cloned into pUC19 downstream of the LacZ gene (23 amino acids) to create a second small fusion gene.

In each instance the IGF gene was amplified from the *E. coli* codon-optimised IGF sequence present in plasmid p10723 (Celtrix Pharmaceuticals, Inc., Glen Allen, Va.) using PCR. pPop and pET29a—PCR primers were designed to incorporate NdeI and BamHI sites at the 5' and 3' termini respectively to facilitate cloning into vector. The 3C protease cleavage site was incorporated immediately downstream of the 5' NdeI site and in-frame with the IGF sequence. pUC19-PCR primers were designed to incorporate Sac and EcoRI sites at the 5' and 3' termini respectively to facilitate cloning into vector. The 3C protease cleavage site was incorporated downstream of the SacI site. The PCR primers are described in the following table:

TABLE 1

PCR primers used to clone 3C-IGF into each of the expression vectors.

| Target | SEQ ID NO: | Primer |
|---|---|---|
| pPop and pET29a | 1 | CATATGCTGGAAGTTCTGTTCCAGGGTCCGGAAACCCTG |
|  | 2 | CCGGGATCCTTAAGCGGATTTAGCCG |
| PUC19 | 3 | GAGCTCGCTGGAAGTTCTGTTCCAA |
|  | 4 | GAATTCTTAAGCGGATTTAGC |

For each 3C-IGF construct, the IGF gene was amplified using the Expand High Fidelity PCR system (Roche Diagnostics Corporation, Indianapolis, Ind.) according to the manufacturers' instructions. In a typical PCR reaction, 2 µls of plasmid DNA were mixed with 5 µls of 10× Expand Buffer containing $MgCl_2$, 1 µl of each primer at 1 µg/µl, 2 µls of 10 mM nucleotide mix and sterile deionised water to a final volume of 50 µls.

The PCR cycle was performed in a thermocycler (Eppendorf Mastercycler, Brinkmann Instruments, Inc.) and included denaturation, annealing and polymerization. The same cycle was used for each PCR. For the first stage of PCR, the template DNA was denatured by heating at 94° C. for 2 minutes. Expand High Fidelity Taq polymerase was added to the reaction mix. In the second stage, the reaction was denatured at 94° C. for 1 minute, cooled to 60° C. for 30 seconds for primer annealing, and heated to 72° C. for 1 minute to enable DNA elongation. Thirty-five subsequent cycles were performed. Following the 35 cycles, a final 10 minute heating step at 72° C. was performed, before cooling the samples to 4° C.

The resulting 3C-IGF PCR product was analyzed by agarose gel electrophoresis. Once satisfied that the PCR product was of the correct size of approximately 230 bp, it was sub-cloned into vector pCR2.1 (Invitrogen Corporation, Carlsbad, Calif.) using the TOPOTA cloning kit (Invitrogen Corporation, Carlsbad, Calif.) according to the manufacturers' instructions. Following ligation, pCR2.1/3C-IGF-1 was transformed into E. coli Top10F' cells (Invitrogen Corporation, Carlsbad, Calif.). Transformants were selected on LB agar containing kanamycin at 50 µg/ml.

Putative 3C-IGF-1 PCR clones were analyzed initially using whole cell lysis preparations to detect the presence of plasmid DNA and its approximate size. Restriction enzyme digestion was performed on the clones to excise the 3C-IGF-1 gene to confirm its presence. NdeI and Bam-HI were used to excise 3C-IGF-1 from sub-clones intended for ligation into pPop. Typically, 18 µls of plasmid DNA was digested with 1 µl of each enzyme in the presence of 2 µls of 10× enzyme specific buffer. The digests were left at 37° C. in a waterbath for 4 hours and electrophoresed on an agarose gel.

The 3C-IGF-1 harboring clones identified above were designated Top10F'::pCR2.1/3C-IGF-1, and Top10F':: pCR2.1/3C-IGF-1(LacZ) and were used to source the 3C-IGF-1 for ligation into pPop, pET29a and pUC19.

B. Ligation of 3C-IGF-1 into pPop and PET29a

Plasmid DNA was isolated from 5 ml overnight cultures of Top10F'::pCR2.1/3C-IGF-1, MSD3363 pPop and XL1-Blue MR::pET29a using the QIAGEN plasmid mini-prep kit (QIAGEN Inc., Valencia, Calif.) according to the manufacturers' instructions. Vectors pPop and pET29a were prepared for ligation to 3C-IGF by digestion with BamHI and NdeI. Similarly, the 3C-IGF gene was excised directly from pCR2.1/3C-IGF-1 by digestion with BamHI and NdeI. The 3C-IGF-1 gene was subsequently ligated overnight to phosphatased pPop and pET29a at 17C using T4 DNA ligase. The resulting constructs, pPop/3C-IGF-1 and pET29a/3C-IGF-1, were transformed into E. coli XL1-Blue MR strain (Stratagene, La Jolla, Calif.) according to the manufacturers' instructions. Transformants were selected using tetracycline resistance for pPop/3C-IGF-I (10 µg/ml), and kanamycin (50 µg/ml) for pET29a/3C-IGF-1.

Transformants were grid plated onto LB agar containing tetracycline (10 µg/ml) for pPop/3C-IGF-1 and kanamycin (50 µg/ml) for pET29a/3C-IGF, and incubated at 37° C. overnight. Clones were analyzed using whole cell lysis preparations and by restriction enzyme digestion with NdeI and BamHI. The resulting constructs which were shown to possess 3C-IGF-1 were designated XL1-Blue MR::pPop/3C-IGF-1 and XL1-Blue MR::pET29a/3C-IGF-1.

C. Ligation of 3C-IGF-1 into pUC19

Plasmid DNA was isolated from a 5 ml overnight cultures of Top10F'::pCR2.1/3C-IGF-1 (LacZ), using the QIAGEN plasmid mini-prep kit (QIAGEN Inc., Valencia, Calif.) according to the manufacturers' instructions. Vector pUC 19 was prepared for ligation to 3C-IGF-1 by digestion with EcoRI and SacI. Similarly, the 3C-IGF-1 gene was excised directly from pCR2.1/3C-IGF-1 (LacZ) by digestion with EcoRI and SacI. The 3C-IGF-1 gene was subsequently ligated overnight to phosphatased pUC19 at 17° C. using T4 DNA ligase. The resulting construct, pUC19/3C-IGF-1, was transformed into E. coli XL1-Blue MR strain (Stratagene) according to the manufacturers' instructions. Transformants were selected using ampicillin resistance (100 µg/ml).

Transformants were grid plated onto LB agar containing ampicillin (100 µg/ml) and incubated at 37° C. overnight. Clones were analysed using whole cell lysis preparations and by restriction enzyme digestion with SacI and EcoRI. The resulting construct which was shown to possess 3C-IGF-1 was designated XL1-Blue MR::pUC19/3C-IGF-1.

D. Electroporation of pPop/3C-IGF-1 and pET29a/3C-IGF-1 into E. coli Host Strains 1 µl each of pPop/3C-IGF-1 and pET29a/3C-IGF-1 from each of the XL1-Blue MR strains harbouring the expression vectors, were electroporated into 5 E. coli DE3 electrocompetent host strains—BL21, MSD68, MSD2252, UT5600 and MSD2254pLysS.

The hosts were electroporated using a Bio-Rad Gene Pulser, according to the manufacturers' instructions (parameters included: 25 µF, 200Ω, 2.5 kV). Transformants harbouring pPop/3C-IGF-1 were selected on LB agar containing 10 µg/ml tetracycline. Transformants harbouring pET29a/3C-IGF-1, were selected on LB agar containing 50 µg/ml kanamycin. The transformants were grid plated out onto LB agar containing appropriate antibiotic and stored at 4° C. Glycerol stocks were made of each strain and stored at −70° C.

E. Expression of 3C-IGF-1 from pPop

Initially, lab-scale shake flasks were used to investigate if 3C-IGF-1 could be expressed from each of the E. coli host strains electroporated with pPop/3C-IGF-1, without being degraded by intracellular proteases (due to the small size of the molecule).

5 mls of LB broth containing 10 μg/ml tetracycline was inoculated with the E. coli host strains harbouring pPop/3C-IGF-1. Cells were grown overnight at 37° C. in an orbital incubator with good aeration (200 rpm). 0.5 mls of each overnight culture was then used to inoculate 50 mls of LB broth containing the 10 μg/ml tetracycline. Cultures were incubated at 37° C. until an OD600 of approximately 0.4-0.6 was obtained. The cultures were induced at this point with 1 mM isopropyl-1-thio-β-D-galactopyranoside (IPTG) for 2.5 hours.

Following induction, both pre- and post-induction samples were electrophoresed to obtain equivalent loadings, on a 4-12% Bis-Tris NuPAGE gel under reduced denatured conditions, according to the manufacturers' instructions No expression of 3C-IGF-1 from any host cell (BL21, MSD68, MSD2252, UT5600 and MSD2254pLysS) was visible on the gel. The results suggest that (a) there was no expression of the protein or (b) the fusion protein was expressed but was degraded by intracellular proteases due to the small size of the fusion. The strength of the promoter/induction makes it highly unlikely that the protein was not expressed, suggesting that the protein was degraded.

F. Ubiguitin-3C-IGF Fusion Gene Construction

The SOE-PCR technique (Warrens et al., Gene 186:29-35 (1997)) was used to clone an existing ubiquitin IGF-I construct (pER10088—Celtrix Pharmaceuticals, Inc., Glen Allen, Va.) into the pPOP expression vector and simultaneously introduce the 3C cleavage sequence between the ubiquitin and the IGF genes. The amino acid sequences of the fusion proteins is shown in FIG. 2

Four plasmids were constructed. Full length ubiquitin (FL) had exactly the same ubiquitin fusion partner as found in pER10088, but with the 6 amino acid 3C recognition site inserted between ubiquitin and the N-terminal of mature IGF-1.

TR41 (truncated at 41) consisted of the first 41 amino acids of ubiquitin followed by the 3C recognition site and IGF-1

TR11 (truncated at 41) consisted of the first 11 amino acids of ubiquitin followed by the 3C recognition site and IGF-1; and TR17 (truncated at 41) consisted of the first 11 amino acids of ubiquitin followed by the 3C recognition site and IGF-1.

Primers were designed to enable cloning into Nde I/Bam HI cut pPop or pET vectors, and purchased from a commercial synthesizer.

Using the primers identified in Table 2, UQ1 and UQ2 produce a full length ubiquitin with a 3C IGF overhang. UQ1 and UQ5 produce a truncated (41 aa) ubiquitin with a 3C IGF overhang. UQ3 and UQ4 produce a 3C IGF with a full length ubiquitin overhang. UQ6 and UQ4 produce a 3C IGF with a truncated ubiquitin overhang. UQ13 and UQ4 produce a truncated (11 aa) ubiquitin with a 3C-IGF overhang. UQ16 and UQ4 produce a truncated (11 aa) ubiquitin with a 3C-IGF overhang.

TABLE 2

SOE-PCR primers used to clone 3C-IGF into each of the expression vectors.

| Primer | SEQ ID NO: | Sequence |
|---|---|---|
| UQ1 | 5 | CATATGCAGATTTTCGTCAAGACTTTGACC |
| UQ4 | 6 | GATCCTTAAGCGGATTTAGCCGGTTTCAG |
| UQ2FL | 7 | GGTTTCCGGACCCTGGAACAGAACTTCCAGACCACCGCGGAG |
| UQ3FL | 8 | CTCCGCGGTGGTCTGGAAGTTCTGTTCCAGGGTCCGGAAACC |
| UQ5TR | 9 | GGTTTCCGGACCCTGGAACAGAACTTCCAGTTGTTGATCTGG |
| UQ6TR | 10 | CCAGATCAACAACTGGAAGTTCTGTTCCAGGGTCCGGAAACC |
| UQ13 | 11 | CATATGCAGATTTTCGTCAAGACTTTGACCGGTAAACTGGAAGTTCTGTTC |
| UQ16 | 12 | CATATGCAGATTTTCGTCAAGACTTTGACCGGTAAAACCATAACATTGGAAGTTCTGGAAGTTCTGTTC |

Using the above primer pairs, PCR was carried out using the Expand High Fidelity PCR system according to the manufacturers' instructions. In each PCR reaction, 2 μls of plasmid DNA (pER10088 or p10724) was mixed with 5 μls of 10× Expand Buffer containing MgCl$_2$, 1 μl of each primer at 1 μg/μl, 2 μls of 10 mM nucleotide mix and sterile deionised water to a final volume of 50 μls.

The PCR cycle was performed in a thermocycler and included denaturation, annealing and polymerization. The same cycle was used for each PCR. For the first stage of PCR, the template DNA was denatured by heating at 94° C. for 2 minutes. Expand High Fidelity Taq polymerase was then added. In the second stage, the reaction was denatured at 94° C. for 1 minute, cooled to 68° C. for 45 seconds for primer annealing, and then heated to 72° C. for 1 minute to enable DNA elongation. 33 subsequent cycles were performed. Next, a final 10 minute heating step at 72° C. was performed, then the samples were cooled to 4° C. (temperature hold).

The PCR products were analyzed by agarosE gel electrophoresis. The bands were excised from the gel and the DNA extracted using a commercial extraction kit (QIAGEN Inc., Valencia, Calif.), and the DNA eluted in 30 μls of buffer.

A second round of PCR was carried out using these PCR products as templates and UQ1 and UQ 4 as primers. The PCR reactions were identical to those used previously except that 1 µl of DNA was used and the annealing temperature was 65° C.

The PCR products were analysed by agarose gel electrophoresis. The bands were excised from the gel and the DNA extracted using a commercial extraction kit, and the DNA eluted in 30 µls of buffer.

3 µls of purified PCR product was sub-cloned into vector pCR2.1 using the TOPOTA cloning kit according to the manufacturers' instructions. Following ligation, the plasmids were transformed into *E. coli* Top10F' cells. Transformants were selected for on LB agar containing kanamycin at 50 µg/ml.

PCR clones were analyzed initially using whole cell lysis preps to detect the presence of plasmid DNA and its approximate size. Restriction enzyme digestion was performed on the clones to excise the 3C-IGF-1 gene to confirm its presence.

NdeI and BamHI were used to excise 3C-IGF-1 from sub-clones intended for ligation into pPop. Typically, 18 µls of plasmid DNA was digested with 1 µl of each enzyme in the presence of 2 µls of 10× enzyme specific buffer. The digests were left at 37° C. in a waterbath for 4 hours and electrophoresed on an agarose gel.

Vector pPop was prepared for ligation by digestion with BamHI and NdeI. The 3C-IGF1 fusions genes were subsequently ligated overnight to phosphatased pPop at 17° C. using T4 DNA ligase. The resulting constructs were transformed into *E. coli* XL1-Blue MR strain according to the manufacturers' instructions. Transformants were selected using tetracycline resistance (10 µg/ml).

Transformants were grid plated onto LB agar containing tetracycline (10 µg/ml) and incubated at 37° C. overnight. Clones were analysed using whole cell lysis preparations and by restriction enzyme digestion with NdeI and BamHI.

Example 2

Creation of *E. coli* Stock by Electroporation

In this example, *E. coli* stock strains harbouring the expression vectors were created by electroporation.

The electrocompetent versions of *E. coli* W3110 and BL21 were electroporated with 1 µl of plasmid DNA isolated from each of the XL1-Blue MR strains harbouring the expression vectors. The hosts were electroporated using a Bio-Rad Gene Pulser, according to the manufacturers' instructions (parameters included: 25 µF, 200Ω, 2.5 kV). Transformants were selected on LB agar containing 10 µg/ml tetracycline. The transformants were grid plated out onto LB agar containing appropriate antibiotic and stored at 4° C. Glycerol stocks were made of each strain and stored at −70° C.

Example 3

Expression of IGF1

Lab-scale shake flasks were used to investigate expression at 37° C. in various host strains.

A. Growth of *E. coli* Stock Strains Harbouring the Expression Vectors 5 mls of LB broth containing the appropriate antibiotic were inoculated with the host strains containing the expression vectors. Cells were grown overnight at 37° C. in an orbital incubator with good aeration. 0.5 mls of each overnight was used to inoculate 50 mls of LB broth containing the appropriate antibiotic. Cultures were incubated at 37° C. until an $OD_{600}$ of approximately 0.4-0.6 was obtained. The cultures were induced at this point with 1 mM isopropyl-1-thio-β-D-galactopyranoside (IPTG) for 2.5 hours.

Following induction, both pre- and post-induction samples were electrophoresed on a 4-12% Bis-Tris NuPAGE gel under reduced denatured conditions, according to the manufacturers' instructions. 1.5 mls of each pre- and post-induction sample were harvested in a benchtop microcentrifuge at 13,000 rpm for 2 minutes. The supernatants were decanted and the pellets re-suspended in deionised water. The amount of water in which each pellet was re-suspended varied and was calculated so as to give suspensions of equivalent optical density so that comparisons between tracks on the gels were meaningful. The loadings on the gels are indicated in brackets after the sample lane. Each gel was quantified using densitometry.

B. Fractionation of Soluble and Insoluble Protein

Cell pellets were harvested by centrifugation at approximately 2,500 g for 10 minutes and re-suspended in one forth of the original volume of 10 mM PBS pH 7.4. The cell suspension was sonicated using a Heat Systems XL2020 sonicator for 7×30 seconds, with 30 seconds cooling between.

The sonicate was harvested by centrifugation at 12,000 rpm (4° C.) for 15 minutes in a Sorvall RC-5B centrifuge. The supernatant (soluble fraction) was decanted and stored on ice. The pellet (insoluble fraction) was re-suspended in 10 mls of sterile deionised water. Samples of each were analyzed on SDS-PAGE gels.

C. Cleavage of the Ubiquitin-IGF Polypeptides with 3C Protease

The different Ubi-3C-IGF-1 fusions constructed as discussed above and Dsb-3C-IGF fusion (p10723—Celtrix Pharmaceuticals, Inc., Glen Allen, Va.), were treated with three different sources of 3C protease.

Shake-flasks preparations were made from two different Dsb3C protease-containing strains. One strain contained a chromosomally integrated 3C protease gene and the other strain carried the 3C protease on a plasmid (Zhang et al., *Protein Expr Purif.* 12:159-165(1998)). Cell free lysates were prepared using sonication followed by centrifugation. A third source of 3C protease was obtained commercially from Amersham Biosciences under the tradename PRECISSION PROTEASE.

The following were mixed in a tube at incubated at room temperature overnight: 2 mls of cell free extract containing IGF fusions, 0.4 mls of cell free extract containing 3C proteases or 5 µls of Prescission protease, 4.8 µls of 0.5 M DTT, and 2.4 µls of 1 M EDTA. Samples were analyzed by SDS-PAGE.

D. Expression of IGF1

1. The Amino Terminus of Ubiquitin Confers High-levels Expression to IGF Fusion Proteins The constructs designed herein were intended to find minimal IGF fusion constructs incorporating a 3C protease cleavage site that yielded high-levels expression in *E. coli* strains. As shown in FIG. 3, Met-3C-IGF and LacZ-3C-IGF did not accumulate to any significant degree upon expression, whereas all ubiquitin-3C-IGF constructs were abundantly expressed. FIG. 4 also demonstrated the relative expression levels of Ubiqutin-IGF, Ubiquitin-3C-IGF, and TR41 Ubi-3C-IGF). Moreover, truncated ubiquitin-3C constructs expressed as-well-as or better than the full length ubiquitin-3C construct. Thus the N-terminal 11 amino acids are sufficient to confer high-level expression of human IGF in E. coli.

2. Truncated Ubiguitin Constructs of IGF Increase the Yield of IGF Protein

As shown in FIG. 3, the truncated ubiquitin constructs provided higher yields of IGF. This is because (1) the relative percentage of IGF is increased as compared to the total fusion protein and (2) because the clones are more efficient at protein expression than the parent ubiquitin-IGF construct. Moreover, because they are exclusively isolated as insoluble proteins, these constructs effectively increase the yield of IGF by reducing the amount of down-stream processing. As is well known in the art, each processing step has a loss associated with it and a corresponding cost associated with the processing. Having the protein exclusively located in one form eliminates the need to process the soluble protein from the cell extract through extra precipitation steps.

Figure 5:
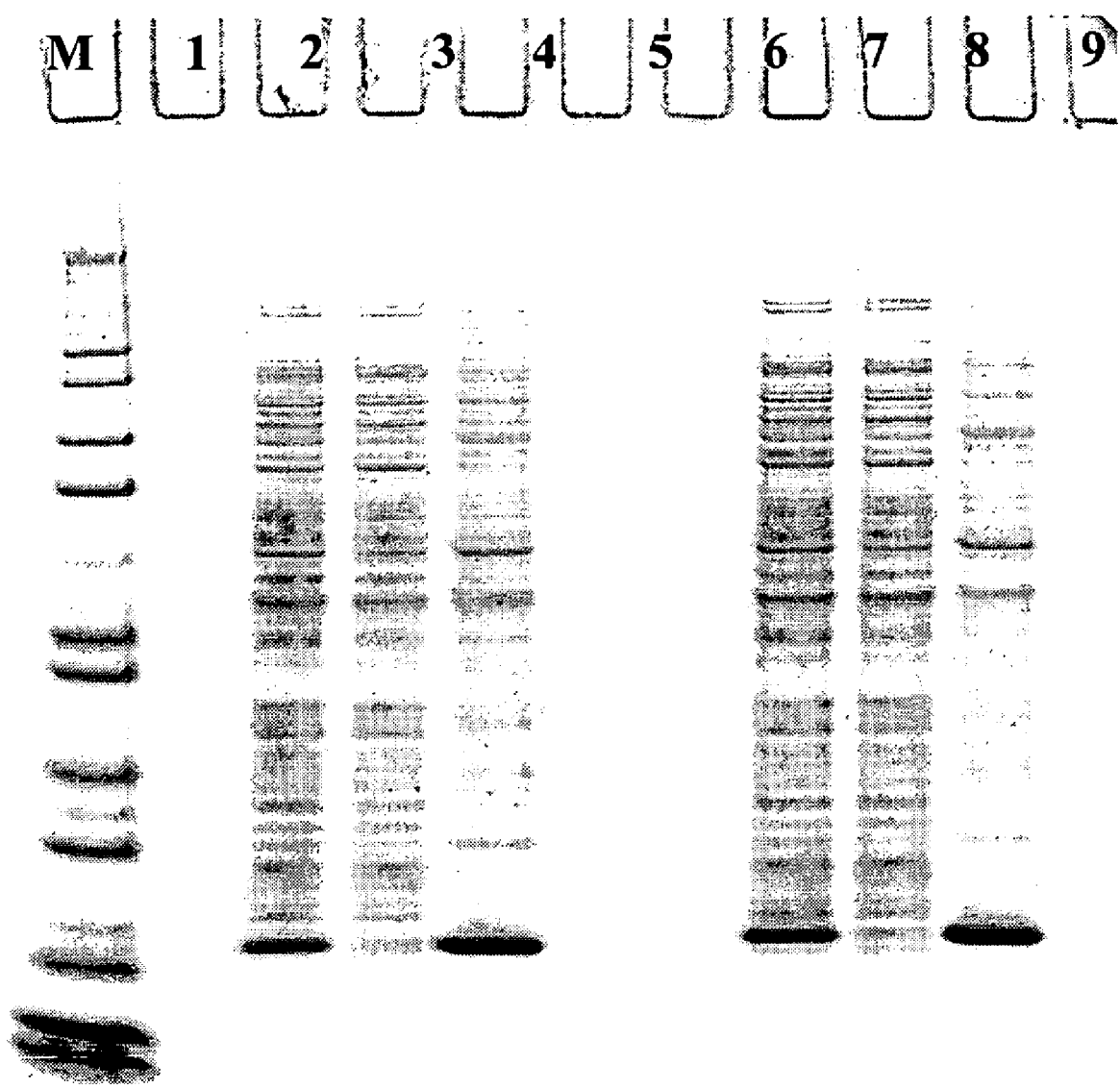
FIG. 5 depicts the soluble and insoluble properties of the TR11 Ubi-3C-IGF and TR17 Ubi-3C-IGF proteins. A SDS-PAGE gel was loaded with the following: (M) molecular weight standards; (1) empty lane; (2) TR11 Ubi-3C-IGF total cell extract; (3) TR11 Ubi-3C-IGF soluble cell extract; (4) TR11 Ubi-3C-IGF insoluble cell extract; (5) empty lane; (6) empty lane; (7) TR17 Ubi-3C-IGF total cell extract; (8) TR17 Ubi-3C-IGF soluble cell extract; and (9) TR11 Ubi-3C-IGF insoluble cell extract.

3. Truncated Ubiquitin Constructs Do Not Possess Ubiquitin-solubilizing Properties FIGS. 4 demonstrates that full-length ubiquitin-3C-IGF is relatively soluble with approximately 50% of the protein in the soluble cell extract and approximately 50% of the protein isolated as insoluble form. Conversely, FIG. 5 shows that TR41 Ubi-3C-IGF and TR11 Ubi-3C-IGF were isolated exclusively in the insoluble form. This allows advantageous isolation of the protein, since the disposition of the protein is exclusively in one form in the cell extract. All three truncated proteins are relatively insoluble and require high concentrations (>4 M Urea) of chaotrope in order to solublize them. In particular, TR11 Ubi-3C-IGF and TR17 Ubi-3C-IGF were more insoluble than TR41 Ubi-3C-IGF, both requiring very high levels (>8M urea) of chaotrope to substantially solubilize the proteins.

Figure 6:
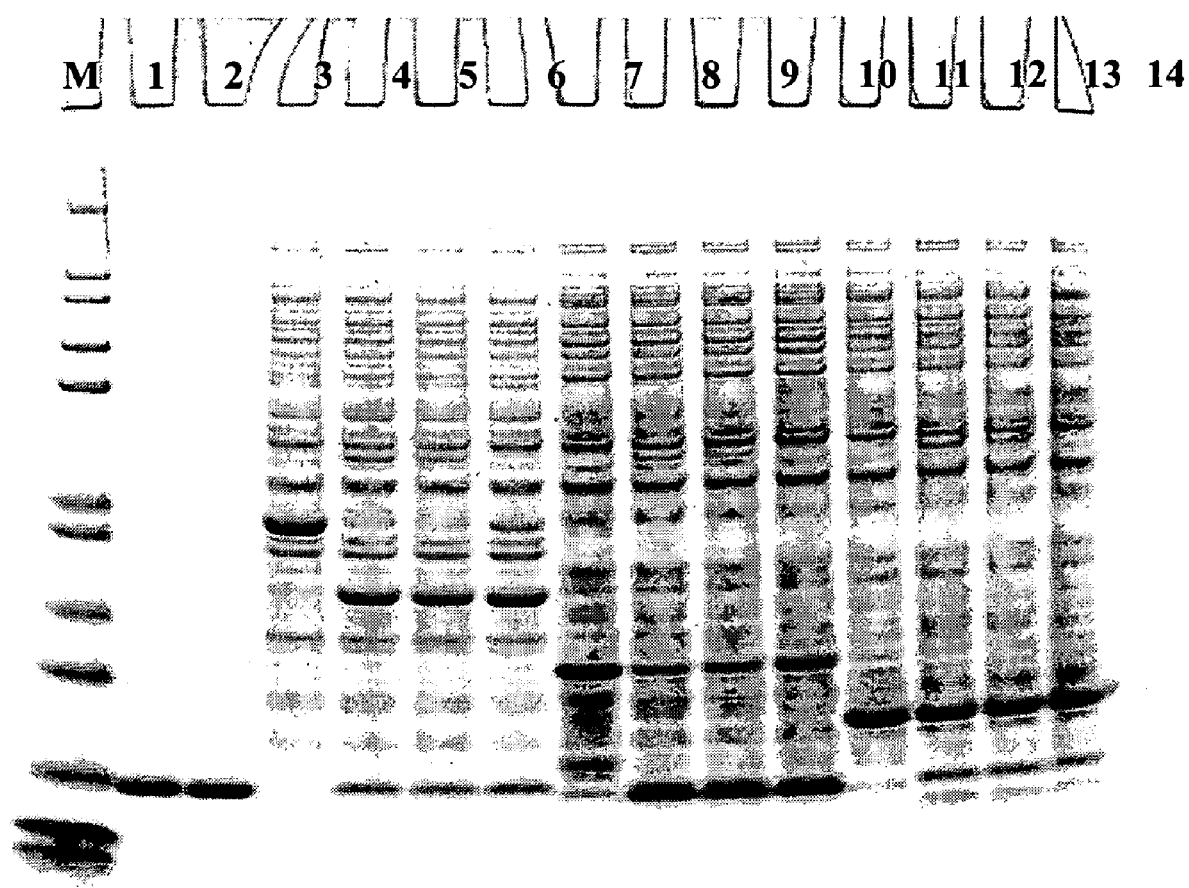
FIG. 6 depicts the relative molecular weights of dsba-3C-IGF, full length Ubiquitin-3C-IGF, and TR41 Ubi-3C-IGF, and the cleavage products, such as mature IGF of these proteins. A SDS-PAGE gel was loaded with the following: (M) molecular weight standards; (1) IGF Standard; (2) IGF Standard; (3) dsbA-3C-IGF cell extract; (4) dsbA-3C-IGF cell extract—3C cleaved; (5) dsbA-3C-IGF cell extract—3C cleaved; (6) dsbA-3C-IGF cell extract—3C cleaved; (7) full length ubiuitin-3C-IGF cell extract; (8) full length ubiuitin-3C-IGF cell extract—3C cleaved; (9) full length ubiuitin-3C-IGF cell extract—3C cleaved; (10) full length ubiuitin-3C-IGF cell extract—3C cleaved; (11) TR41 Ubi-3C-IGF cell extract; (12) TR41 Ubi-3C-IGF cell extract—3C cleaved; (13) TR41 Ubi-3C-IGF cell extract—3C cleaved; and (14) TR41 Ubi-3C-IGF cell extract—3C cleaved.

4. Truncated Ubiquitin Constructs of IGF are Cleaved by 3C Protease to Yield Mature IGF with the Correct N-terminus FIG. 6 demonstrates dsbA-3C-IGF, full length ubiquitin-3C-IGF, and TR41 Ubi-3C-IGF cleavage by three different sources of 3C protease (as described in Example 3C, above). In each case, the IGF is liberated as seen by comparison of the band corresponding with the same molecular weight of the IGF standard. Note that the cleavage of dsbA-3C-IGF and TR41 Ubi-3C-IGF is essentially quantitative, while the full length ubiquitin-3C-IGF has some uncleaved product. The experiment was not optimized for cleavage conditions. Thus, the lack of quantitative cleavage does not negatively reflect on the quality of the construct. In a single experiment of TR11 Ubi-3C-IGF and TR17 Ubi-3C-IGF, these constructs were not cleaved by 3C protease at all. The inventors determined, however, that the amount of chaotrope in the reaction inactivated the enzyme. It is likely that these constructs would be cleaved by the 3C protease if the basal solution was sufficiently free of interfering chaotrope.

N-terminal amino acid sequencing was conducted on the IGF isolated from 3C protease cleaved TR41 Ubi-3C-IGF and the mature IGF demonstrated the correct N-terminus sequence for human IGF.

The invention has been disclosed broadly and illustrated in reference to representative embodiments described above. Those skilled in the art will recognize that various modifications can be made to the present invention without departing from the spirit and scope thereof.

We claim:

1. An isolated nucleic acid sequence encoding a polypeptide comprising the following sequence:

MQIFVKTLTGK[$X^1$]LE[$X^2$]LFQ[IGF]    (SEQ ID NO: 23)

wherein $X^1$ is a polypeptide having a sequence from 0 to 30 amino acids; $X^2$ is either V or T; and wherein the C-terminus of said polypeptide is fused to IGF.

2. The nucleic acid of claim 1, wherein $X^1$ is selected from the group consisting of (A) zero amino acids, (B) six amino acids of the sequence TITLEV (SEQ ID NO: 24) and (C) 30 amino acids of the sequence

TITLEVESSDTIDNVKSKIQDKEGIPPDQQ.    (SEQ ID NO: 25)

3. A protein expression system, comprising a protein expression vector encoding the protein

MQIFVKTLTGK[$X^1$]LE[$X^2$]LFQ[IGF]    (SEQ ID NO: 23)

wherein $X^1$ is a polypeptide having a sequence from 0 to 30 amino acids; $X^2$ is either V or T; and wherein the C-terminus of said polypeptide is fused to IGF.

4. The protein expression system of claim 3, wherein $X^1$ is selected from the group consisting of (A) zero amino acids, (B) six amino acids of the sequence TITLEV (SEQ ID NO: 24) and (C) 30 amino acids of the sequence

TITLEVESSDTIDNVKSKIQDKEGIPPDQQ.    (SEQ ID NO: 25)

5. A protein expression system, comprising a host cell and a protein expression vector encoding the polypeptide

MQIFVKTLTGK[$X^1$]LE[$X^2$]LFQ[IGF]    (SEQ ID NO: 23)

wherein $X^1$ is a polypeptide having a sequence from 0 to 30 amino acids; $X^2$ is either V or T; and wherein the C-terminus of said polypeptide is fused to IGF.

6. The protein expression system of claim 5, wherein $X^1$ is selected from the group consisting of (A) zero amino acids, (B) six amino acids of the sequence TITLEV (SEQ ID NO: 24) and (C) 30 amino acids of the sequence

TITLEVESSDTIDNVKSKIQDKEGIPPDQQ.    (SEQ ID NO: 25)

7. The protein expression system of claim 5, wherein the host cell is prokaryotic.

8. The protein expression system of claim 5, wherein the host cell is eukaryotic.

9. A method of expressing IGF comprising:
(A) transfecting a host cell with an expression vector encoding the polypeptide

MQIFVKTLTGK[$X^1$]LE[$X^2$]LFQ[IGF]    (SEQ ID NO: 23)

wherein $X^1$ is a polypeptide having a sequence from 0 to 30 amino acids; $X^2$ is either V or T; and wherein the C-terminus of said polypeptide is fused to IGF.
(B) culturing said host cell under conditions that permit expression of said polypeptide; and
(C) isolating the polypeptide.

10. The method of claim 9, wherein $X^1$ is selected from the group consisting of (A) zero amino acids, (B) six amino acids of the sequence TITLEV (SEQ ID NO: 24) and (C) 30 amino acids of the sequence

TITLEVESSDTIDNVKSKIQDKEGIPPDQQ.    (SEQ ID NO: 25)

11. The method of claim 9, wherein the host cell is prokaryotic.

12. The method of claim 9, wherein the host cell is eukaryotic.

13. An isolated nucleic acid sequence encoding a polypeptide comprising the polypeptide of SEQ ID NO: 23 and IGF, wherein the C-terminus of SEQ ID NO: 23 is fused to IGF.

* * * * *

SEQUENCE LISTING

<160> NUMBER OF SEQ ID NOS: 26

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
catatgctgg aagttctgtt ccagggtccg gaaaccctg                          39

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccgggatcct taagcggatt tagccg                                        26

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 3
gagctcgctg gaagttctgt tccaa                                             25

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gaattcttaa gcggatttag c                                                 21

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
catatgcaga ttttcgtcaa gactttgacc                                        30

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatccttaag cggatttagc cggtttcag                                         29

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggtttccgga ccctggaaca gaacttccag accaccgcgg ag                          42

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctccgcggtg gtctggaagt tctgttccag ggtccggaaa cc                          42

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 9
ggtttccgga ccctggaaca gaacttccag ttgttgatct gg                              42

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccagatcaac aactggaagt tctgttccag ggtccggaaa cc                              42

<210> SEQ ID NO 11
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
catatgcaga ttttcgtcaa gactttgacc ggtaaactgg aagttctgtt c                    51

<210> SEQ ID NO 12
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
catatgcaga ttttcgtcaa gactttgacc ggtaaaacca taacattgga agttctggaa           60
gttctgttc                                                                  69

<210> SEQ ID NO 13
<211> LENGTH: 213
<212> TYPE: DNA
<213> ORGANISM: Homo sapiens

<400> SEQUENCE: 13
ggtccggaaa ccctgtgcgg tgctgaactg gttgacgctc tgcagttcgt ttgcggtgac           60
cgtggtttct acttcaacaa accgaccggt tacggttcct cctcccgtcg tgctccgcag          120
accggtatcg ttgacgaatg ctgcttccgg tcctgcgacc tgcgtcgtct ggaaatgtac          180
tgcgctccgc tgaaaccggc taaatccgct taa                                      213

<210> SEQ ID NO 14
<211> LENGTH: 77
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 14

Met Leu Glu Val Leu Phe Gln Gly Pro Glu Thr Leu Cys Gly Ala Glu
 1               5                  10                  15

Leu Val Asp Ala Leu Gln Phe Val Cys Gly Asp Arg Gly Phe Tyr Phe
            20                  25                  30

-continued

```
Asn Lys Pro Thr Gly Tyr Gly Ser Ser Arg Arg Ala Pro Gln Thr
        35                  40                  45

Gly Ile Val Asp Glu Cys Cys Phe Arg Ser Cys Asp Leu Arg Arg Leu
    50                  55                  60

Glu Met Tyr Cys Ala Pro Leu Lys Pro Ala Lys Ser Ala
65                  70                  75

<210> SEQ ID NO 15
<211> LENGTH: 100
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 15

Met Ile Thr Pro Ser Leu His Ala Cys Arg Phe Ser Thr Leu Glu Asp
1               5                   10                  15

Pro Arg Val Pro Ser Ser Asn Ser Leu Glu Val Leu Phe Gln Gly Pro
                20                  25                  30

Glu Thr Leu Cys Gly Ala Glu Leu Val Asp Ala Leu Gln Phe Val Cys
            35                  40                  45

Gly Asp Arg Gly Phe Tyr Phe Asn Lys Pro Thr Gly Tyr Gly Ser Ser
        50                  55                  60

Ser Arg Arg Ala Pro Gln Thr Gly Ile Val Asp Glu Cys Cys Phe Arg
65                  70                  75                  80

Ser Cys Asp Leu Arg Arg Leu Glu Met Tyr Cys Ala Pro Leu Lys Pro
                85                  90                  95

Ala Lys Ser Ala
        100

<210> SEQ ID NO 16
<211> LENGTH: 146
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 16

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Gly Gly Pro Glu Thr
65                  70                  75                  80

Leu Cys Gly Ala Glu Leu Val Asp Ala Leu Gln Phe Val Cys Gly Asp
                85                  90                  95

Arg Gly Phe Tyr Phe Asn Lys Pro Thr Gly Tyr Gly Ser Ser Ser Arg
            100                 105                 110

Arg Ala Pro Gln Thr Gly Ile Val Asp Glu Cys Cys Phe Arg Ser Cys
        115                 120                 125
```

```
Asp Leu Arg Arg Leu Glu Met Tyr Cys Ala Pro Leu Lys Pro Ala Lys
            130                 135                 140

Ser Ala
145
```

```
<210> SEQ ID NO 17
<211> LENGTH: 152
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 17

Met Gln Ile Phe Val Lys Thr Leu Thr Gly Lys Thr Ile Thr Leu Glu
  1               5                  10                  15

Val Glu Ser Ser Asp Thr Ile Asp Asn Val Lys Ser Lys Ile Gln Asp
             20                  25                  30

Lys Glu Gly Ile Pro Pro Asp Gln Gln Arg Leu Ile Phe Ala Gly Lys
         35                  40                  45

Gln Leu Glu Asp Gly Arg Thr Leu Ser Asp Tyr Asn Ile Gln Lys Glu
 50                  55                  60

Ser Thr Leu His Leu Val Leu Arg Leu Arg Gly Gly Leu Glu Val Leu
 65                  70                  75                  80

Phe Gln Gly Pro Glu Thr Leu Cys Gly Ala Glu Leu Val Asp Ala Leu
                 85                  90                  95

Gln Phe Val Cys Gly Asp Arg Gly Phe Tyr Phe Asn Lys Pro Thr Gly
            100                 105                 110

Tyr Gly Ser Ser Ser Arg Arg Ala Pro Gln Thr Gly Ile Val Asp Glu
        115                 120                 125

Cys Cys Phe Arg Ser Cys Asp Leu Arg Arg Leu Glu Met Tyr Cys Ala
    130                 135                 140

Pro Leu Lys Pro Ala Lys Ser Ala
145                 150
```

```
<210> SEQ ID NO 18
<211> LENGTH: 117
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 18

Met Gln Ile Phe Val Lys Thr Leu Thr Gly Lys Thr Ile Thr Leu Glu
  1               5                  10                  15

Val Glu Ser Ser Asp Thr Ile Asp Asn Val Lys Ser Lys Ile Gln Asp
             20                  25                  30

Lys Glu Gly Ile Pro Pro Asp Gln Gln Leu Glu Val Leu Phe Gln Gly
         35                  40                  45

Pro Glu Thr Leu Cys Gly Ala Glu Leu Val Asp Ala Leu Gln Phe Val
 50                  55                  60

Cys Gly Asp Arg Gly Phe Tyr Phe Asn Lys Pro Thr Gly Tyr Gly Ser
 65                  70                  75                  80

Ser Ser Arg Arg Ala Pro Gln Thr Gly Ile Val Asp Glu Cys Cys Phe
                 85                  90                  95
```

```
Arg Ser Cys Asp Leu Arg Arg Leu Glu Met Tyr Cys Ala Pro Leu Lys
                100                 105                 110

Pro Ala Lys Ser Ala
        115

<210> SEQ ID NO 19
<211> LENGTH: 93
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 19

Met Gln Ile Phe Val Lys Thr Leu Thr Gly Lys Thr Ile Thr Leu Glu
  1               5                  10                  15

Val Leu Glu Val Leu Phe Gln Gly Pro Glu Thr Leu Cys Gly Ala Glu
                 20                  25                  30

Leu Val Asp Ala Leu Gln Phe Val Cys Gly Asp Arg Gly Phe Tyr Phe
             35                  40                  45

Asn Lys Pro Thr Gly Tyr Gly Ser Ser Arg Arg Ala Pro Gln Thr
         50                  55                  60

Gly Ile Val Asp Glu Cys Cys Phe Arg Ser Cys Asp Leu Arg Arg Leu
 65                  70                  75                  80

Glu Met Tyr Cys Ala Pro Leu Lys Pro Ala Lys Ser Ala
                 85                  90

<210> SEQ ID NO 20
<211> LENGTH: 87
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 20

Met Gln Ile Phe Val Lys Thr Leu Thr Gly Lys Leu Glu Val Leu Phe
  1               5                  10                  15

Gln Gly Pro Glu Thr Leu Cys Gly Ala Glu Leu Val Asp Ala Leu Gln
                 20                  25                  30

Phe Val Cys Gly Asp Arg Gly Phe Tyr Phe Asn Lys Pro Thr Gly Tyr
             35                  40                  45

Gly Ser Ser Ser Arg Arg Ala Arg Gln Thr Gly Ile Val Asp Glu Cys
         50                  55                  60

Cys Phe Arg Ser Cys Asp Leu Arg Arg Leu Glu Met Tyr Cys Ala Pro
 65                  70                  75                  80

Leu Lys Pro Ala Lys Ser Ala
                 85

<210> SEQ ID NO 21
<211> LENGTH: 70
<212> TYPE: PRT
<213> ORGANISM: Homo sapiens

<400> SEQUENCE: 21

Gly Pro Glu Thr Leu Cys Gly Ala Glu Leu Val Asp Ala Leu Gln Phe
  1               5                  10                  15

Val Cys Gly Asp Arg Gly Phe Tyr Phe Asn Lys Pro Thr Gly Tyr Gly
                 20                  25                  30
```

```
Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
 65                  70

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Val or Thr

<400> SEQUENCE: 22

Glu Xaa Leu Phe Gln Gly Pro
 1               5

<210> SEQ ID NO 23
<211> LENGTH: 47
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(41)
<223> OTHER INFORMATION: This region may encompass 0-30 variable amino
      acids, the peptide disclosed as SEQ ID NO: 24, or
      the peptide disclosed as SEQ ID NO: 25.
<220> FEATURE:
<221> NAME/KEY: MOD_RES
<222> LOCATION: (44)
<223> OTHER INFORMATION: Val or Thr

<400> SEQUENCE: 23

Met Gln Ile Phe Val Lys Thr Leu Thr Gly Lys Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Leu Glu Xaa Leu Phe Gln
        35                  40                  45

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Ile Thr Leu Glu Val
 1               5

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 25

Thr Ile Thr Leu Glu Val Glu Ser Ser Asp Thr Ile Asp Asn Val Lys
  1               5                   10                  15

Ser Lys Ile Gln Asp Lys Glu Gly Ile Pro Pro Asp Gln Gln
             20                  25                  30

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Val or Thr

<400> SEQUENCE: 26

Glu Xaa Leu Phe Gln
  1               5
```